(12) United States Patent
Bowman et al.

(10) Patent No.: US 10,508,116 B2
(45) Date of Patent: Dec. 17, 2019

(54) CLICK NUCLEIC ACID POLYMERS AND METHODS OF USE

(71) Applicant: THE REGENTS OF THE UNIVERSITY OF COLORADO, A BODY CORPORATE, Denver, CO (US)

(72) Inventors: Christopher N. Bowman, Boulder, CO (US); Weixian Xi, Pasadena, CA (US); Sankha Pattanayak, Mountain View, CA (US)

(73) Assignee: THE REGENTS OF THE UNIVERSITY OF COLORADO, A BODY, Denver, CO (US)

( * ) Notice: Subject to any disclaimer, the term of this patent is extended or adjusted under 35 U.S.C. 154(b) by 186 days.

(21) Appl. No.: 15/726,419

(22) Filed: Oct. 6, 2017

(65) Prior Publication Data

US 2018/0100036 A1    Apr. 12, 2018

Related U.S. Application Data

(60) Provisional application No. 62/405,519, filed on Oct. 7, 2016.

(51) Int. Cl.
| | | |
|---|---|---|
| *C07D 473/34* | (2006.01) | |
| *C08G 75/045* | (2016.01) | |
| *C12N 15/113* | (2010.01) | |
| *C07D 239/47* | (2006.01) | |
| *C07D 473/18* | (2006.01) | |
| *C07D 239/54* | (2006.01) | |

(Continued)

(52) U.S. Cl.
CPC ......... *C07D 473/34* (2013.01); *C07D 239/47* (2013.01); *C07D 239/54* (2013.01); *C07D 473/18* (2013.01); *C08G 75/00* (2013.01); *C08G 75/045* (2013.01); *C12N 15/113* (2013.01); *C12Q 1/6876* (2013.01); *C12N 2310/11* (2013.01); *C12N 2310/318* (2013.01)

(58) Field of Classification Search
CPC .. C07D 473/34; C07D 473/18; C07D 239/54; C07D 239/47; C12Q 1/6876
USPC ........................................................ 536/23.1
See application file for complete search history.

(56) References Cited

U.S. PATENT DOCUMENTS

| 6,075,143 A | 6/2000 | Breiphohl et al. |
| 2009/0124534 A1 | 5/2009 | Reineke |
| 2011/0077407 A1 | 3/2011 | David et al. |

(Continued)

FOREIGN PATENT DOCUMENTS

| CA | 2078256 A1 | 3/1994 |
| JP | 258222 A | 10/1995 |

(Continued)

OTHER PUBLICATIONS

Japanese Office Action issued in JP Patent Application No. 2015-503259 dated Oct. 18, 2016, with English translation of same (16 pages).

(Continued)

*Primary Examiner* — Jezia Riley
(74) *Attorney, Agent, or Firm* — FisherBroyles, LLP; Richard Echler; Jason M. Pass (57) ABSTRACT

Disclosed herein are Click Nucleic Acid Polymers (CNA-polymers) that comprise repeating dimer, trimer and tetramer units. The disclosed polymers can be used for antisense applications, for example, in treatment of "trinucleotide repeat disorders, i.e., Huntington's Disease and the like.

20 Claims, 2 Drawing Sheets

(51) Int. Cl.
*C12Q 1/6876* (2018.01)
*C08G 75/00* (2006.01)

(56) References Cited

U.S. PATENT DOCUMENTS

| | | | |
|---|---|---|---|
| 2011/0129921 A1 | 6/2011 | Johnson et al. |
| 2011/0171448 A1 | 7/2011 | Tang et al. |
| 2012/0071641 A1 | 3/2012 | Manoharan et al. |

FOREIGN PATENT DOCUMENTS

| | | |
|---|---|---|
| WO | 1989012060 A1 | 12/1989 |
| WO | 1995031470 A2 | 11/1995 |
| WO | 199604295 A1 | 2/1996 |
| WO | 2010048549 A2 | 4/2010 |

OTHER PUBLICATIONS

Hoyle et al., "Thiol-click chemistry: a multifaceted toolbox for small molecule and polymer synthesis", Chem Soc Rev. Apr. 2010;39(4):1355-87. doi: 10.1039/b901979k. Epub Feb. 9, 2010.
Zhang et al., "Synthesis and hybridization property of an oligonucleotide containing a 3-thioformacetal linked pentathymidylate", Bioorg Med Chem Lett. Feb. 8, 1999;9(3):319-22.
Chinese Office Action issued in CN Patent Application No. 201380024075.7 dated Feb. 14, 2017, with English translation of same (13 pages).
Image File Wrapper of U.S. Appl. No. 14/388,748, filed Sep. 26, 2014, First Named Inventor Christopher N. Bowman (264 pages).
Konkolewicz et al., "Hyperbranched polymers by thiol-yne chemistry: from small molecules to functional polymers", J Am Chem Soc. Dec. 23, 2009;131(50):18075-7. doi: 10.1021/ja908206a.
English Translation of Second Office Action issued Jun. 20, 2016, in Chinese Patent Application No. CN 201380024075.7 (9 pages).
Communication Pursuant to Rules 70(2) and 70a(2) EPC issued Jun. 17, 2016 in European Patent Application No. 13767244.0 (1 page).
Extended European Search Report dated May 31, 2016 in European Patent Application No. 13767244.0 (9 pages).
Dose et al., "Convergent synthesis of peptide nucleic acids by native chemical ligation", Org Lett. Sep. 29, 2005;7(20):4365-8.
Gogoi et al., "Sugar-thioacetamide backbone in oligodeoxyribonucleosides for specific recognition of nucleic acids", Chem Commun (Camb). Jun. 14, 2006;(22):2373-5. Epub Apr. 25, 2006.
Nielsen et al. "Sequence-Selective Recognition of DNA by Strand Displacement with a Thymne-Substituted Polyamide," Science Reports, vol. 254. pp. 1497-1500 (1991).
Scheibe et al., "DNA-programmed spatial screening of carbohydrate-lectin interactions", Chemical Science, vol. 2., No. 4, Jan. 1, 2011 (Jan. 1, 2011) p. 770, XP055272631, United Kingdom, ISSN: 2041-6520, DOI: 10.1039/c0c00565g.
Mourtas et al., "S-4 Methoxytrityl Mercapto Acids: Synthesis and Application," Tetrahedron Letters, vol. 42, Issue 39, Sep. 24, 2001, pp. 6965-6967.
PubChem Record CID 2245987, URL: http://pubchem.ncbi.nlm.nih.gov/summary/summary.cgi?cid=2245987, Create Date: Jul. 15, 2005, Accessed: Apr. 13, 2013, pp. 1-3.
PubChem Record CID 201366, URL: http://pubchem.ncbi.nlm.nih.gov/summary/summary.cgi?cid=201366, Create Date: Aug. 9, 2005, Accessed: Apr. 13, 2013, pp. 1-3.
PubChem Record CID 5232652, URL: http://pubchem.ncbi.nlm.nih.gov/summary/summary.cgi?cid=5232652, Create Date: Oct. 7, 2005, Accessed: Apr. 13, 2013, pp. 1-3.
EP 12 746 630.1 Thiol-X Click Foldamers for Polymer Affinity and Catalysis Libraries; Extended European Search Report dated Jun. 8, 2017, for corresponding European Application.
U.S. Appl. No. 14/388,748 Click Nucleic Acids Notice of Allowance dated Sep. 13, 2017.
JP 2015-503259 Click Nucleic Acids; Decision to Grant dated Sep. 5, 2017 (Japanese). Allowed Claims attached herewith.
CN 201380024075.7 Click Nucleic Acids; Office Action dated Feb. 14, 2017.
European Office Action, European Patent Application No. EP 13 767 244.0, dated Apr. 23, 2018.
Canadian Office Action, Canadian Application No. 2,938,875, dated Dec. 1, 2017.
Response to European Office Action, European Patent Application No. EP 15 746 630.1, dated Dec. 21, 2017.
Notice of Allowance U.S. Appl. No. 14/388,748, Allowed Claims Attached, dated 2017.
Chinese Office Action issued in CN Patent Application No. 201380024075.7 dated Sep. 6, 2015, English translation (8 pages).
Pensato et al. "New Synthetic Route to gamma-Mercaptomethyl PNA Monomers," Synthetic Communications, 38 2499-2506 (2008).

CLICK NUCLEIC ACID POLYMERS AND METHODS OF USE

FIELD OF THE DISCLOSURE

Disclosed herein are Click Nucleic Acid Polymers (CNA-polymers) that comprise repeating dimer, trimer and tetramer units. The disclosed polymers can be used for antisense applications, for example, in treatment of "tri-nucleotide repeat disorders, i.e., Huntington's Disease and the like.

DETAILED DESCRIPTION

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

The term "residue" means an element of an oligomer or polymer that derives from a monomer. For example, below is a residue and the monomer from which the residue is derived.

Huntington Disease (HD) has the highest occurrence among all CAG repeat neurodegenerative diseases with an incidence of 1 per 10,000 individuals. HD is caused by mutant huntington (HTT) protein. This mutation occurs as an expansion of a trinucleotide CAG repeat within the mutant HTT allele that is responsible for the formation of neurotoxic polyglutamine tract in the mutant HTT protein. Unaffected individuals have an average of 20 CAG repeats whereas 45 repeats are average in case of HD patients. The symptoms of HD include cognitive impairment, violent choreiform movement (ballism), severe mood and behavioral disorders that are chronic and progressive till the inevitable death. Until now, no curative treatment is available for HD patents.

Most of the conventional therapies involving small-molecule drugs are designed to target proteins (GPCR, enzymes etc) to heal a particular disease and thus intrinsic genetic diseases remained largely 'undruggable' by those approaches. Advancement of molecular genetics in recent years have identified antisense oligonucleotides (ASOs) as very attractive tools to act as targeted therapy for various life-threatening genetic (and non-genetic) diseases and represent about half of the active clinical trials currently in the United States. ASOs are short (~25 mer) synthetic DNA-based molecules having favorable properties like strong sequence-specific binding with target gene, enzyme-stability, non-toxicity and ability to perturb protein synthesis by a variety of mechanism. Moreover, synthetic oligonucleotides such as DNA, RNA, and PNA have continued to find ever-increasing levels of implementation and exciting applications in biology and biomedical systems, whether for as aptamers, for drug delivery and targeting, in biodetection, and in many other areas.

Genomic analyses, however, have shown that abnormal expansions of simple repeating sequences in the genome are responsible for a wide class of genetic disorders. At least 16 human-inherited neurological diseases are caused by simple trinucleotide repeat expansions (CAG, CUG etc.) that are collectively known as trinucleotide repeat disorder. This class of diseases includes Huntington disease (caused by CAG repeat), myotonic dystrophy type 1 (caused by CUG repeat), Fragile X syndrome (caused by CGG repeat) and several types of ataxia. Additionally, expanded hexanucleotide (GGGGCC) repeat in C9ORF72 gene has been identified as the cause for amyotrophic lateral sclerosis (ALS), Alzheimer's disease and frontotemporal dementia. The telomere is also consists of repeat sequences of TTAGGG, which is a lucrative cancer target. ASO-based approaches targeting these sequences showed promising results to treat the corresponding diseases. Notably, even if the sequences are repetitive in nature, by conventional solid phase synthesis the targeting ASO can only be prepared using step-by-step fashion that require the same efforts and resources like the synthesis of a complex sequence.

The present disclosure relates to CNA (Click Nucleic Acid) polymers which can be assembled under facile and controlled processes. Use of the two reactions disclosed, the thiol-Michael and thiol-ene reactions, allow the formulator to prepare unequivocal compositions of varying desired length.

Disclosed herein are monomers which can be assembled into oligomers having two or more residues. Subsequently the oligomers can be polymerized to afford CNA-polymers having repeating sequences of the desired oligomers.

Two distinct types of monomers are disclosed. Monomers of Type A are capable of reacting with one another to form the expanding chain of the disclosed oligomers (thiol-Michael monomers). Type B monomers serve as the anchoring unit for the oligomers and are capable of serving as the "ene receptor" in Click-type polymerizations (thiol-ene monomers).

Type A Monomers

Type A monomers have the general formula:

wherein NB is a nucleobase, for example, cytosine. When the thiol group is suitably protected, the vinyl moiety can undergo an ene-Michael type addition from with the thiol group of a Type A or Type B comprising monomer or growing oligomer.

Type B Monomers

Type B monomers have the general formula:

wherein NB is a nucleobase, for example, cytosine. Type B monomers can react with thiol protected Type A monomers via an ene-Michael addition. Type B monomers can further react with an unprotected thiol moiety to undergo a thiol-ene polymerization.

The following schemes illustrate the formation of oligomers and CNA-polymers. The scheme below represents the first step in forming the disclosed oligomers.

A unprotected thiol Type B monomer undergoes a thiol-Michael addition to a protected Type A monomer. After de-protection of the Type A thiol, the dimer is further reacted under ene-Michael conditions with a thiol protected Type A monomer to afford the terminal thiol protected trimer having the formula:

Once the desired dimer, trimer, tetramer, etc., is formed, the terminal thiol group is de-protected and the resulting oligomer is polymerized under Click thiol-ene conditions, for example, to form the polymer having the formula:

The value of the index n can be from about 1 to about 100, however, the formulator can obtain CNA-polymers having any desired length.

As such, the disclosed CNA-polymers have the formula:

wherein each NB is the same or different nucleobase, the index m is an integer from 0 to 20 and the index n is an integer from 0 to about 100. The nucleobase can be any naturally occurring or synthetic nucleobase. Non-limiting examples of nucleobases include cytosine, guanine, adenine, thymine, uracil, 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, β-D-galactosyl-queosine, inosine, 1-methylguanine, 1-methylinosine, 2,2-dimethylguanine, 2-methyladenine, 2-methylguanine, 3-methylcytosine, 5-methyl-cytosine, $N^6$-adenine, 7-methylguanine, 5-methylaminomethyluracil, methoxyamino-methyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid, pseudo-uracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-$N^2$-carboxypropyl)uracil, and 2,6-diaminopurine.

One aspect of the disclosure relates to CNA-polymers wherein the nucleobases are chosen from cytosine, guanine, adenine, thymine, or uracil. In another aspect the nucleobases are chosen from cytosine, guanine, adenine, or thymine. In a further aspect the nucleobases are chosen from cytosine, guanine, adenine, or uracil.

One aspect of the disclosed CNA-polymers relates to polymers comprising trimers, for example, CNA-polymers having the formula:

wherein the index n is an integer from 0 to about 20. One iteration of the disclosed CNA-polymers relates to polymers comprising an oligomer having the GUC antisense codon having the formula:

which can be used for the treatment of CAG repeat diseases, for example, Huntington's disease.

Another iteration of the disclosed I-polymers relates to polymers comprising an oligomer having the GTC antisense codon having the formula:

which can be used for the treatment of CUG repeat diseases, for example, myotonic dystrophy type 1.

A further iteration of the disclosed CNA-polymers relates to polymers comprising an oligomer having the GTC antisense codon having the formula:

which can be used for the treatment of CGG repeat diseases, for example, Fragile X syndrome and several types of ataxia.

The value of the index m can be any value from 0 to 20. In one embodiment the index m is an integer from 1 to 5. In another embodiment the index m is an integer from 1 to 4. In a further embodiment the index m is an integer from 1 to 3. In a yet further embodiment the index m is an integer from 1 to 2. The index m can have any value from 0 to 20, for example, 0, 1, 2, 3, 4, 5, 6, 7, 8, 9, 10, 11, 12, 13, 14, 15, 16, 17, 18, 19, or 20.

As stated herein above, the value of the index n can be an integer from 0 to about 100. In one embodiment the index n is an integer from about 1 to about 100. In another embodiment the index n is an integer from about 1 to about 50. In a further embodiment the index n can be an integer from about 1 to about 20. In a still further embodiment the index n can be an integer from about 1 to about 10. In a yet another embodiment the index n can be an integer from about 1 to about 8. In a still yet another embodiment the index n can be an integer from about 1 to about 6. In a still yet further embodiment the index n can be an integer from about 1 to about 4. In one embodiment the index m can have any of the following values from 0 to 20, for example, 0, 1, 2, 3, 4, 5, 6, 7, 8, 9, 10, 11, 12, 13, 14, 15, 16, 17, 18, 19, or 20.

Type C Monomers

Type C monomers have the general formula:

wherein NB is a nucleobase, for example, cytosine. Type C monomers can react with thiol de-protected Type A monomers via an ene-Michael addition. Type C monomers can further react with an unprotected thiol moiety to undergo a thiol-ene reactions. The scheme below is an example of a Type C monomer reacting via thiol-ene reaction with a Type D/Type A dimer.

Type D Monomers

Type D monomers have the general formula:

wherein NB is a nucleobase, for example, cytosine. Type C monomers can react with thiol protected Type A monomers via an ene-Michael addition. The scheme below is an example of a Type D monomer reacting with a Type B/Type D dimers.

PREPARATION

Scheme I below outlines the preparation of a non-limiting example of a Type B monomer (thiol-ene) as described in Example 1.

Scheme I

Reagents and conditions: trityl chloride, TFA;. rt. 3 hr

Reagents and conditions: TEA, THF; rt, 18 hr.

3

Reagents and conditions: EDC, HOBt; rt, 18 hr.

Example 1

N-allyl-2-(5-methyl-2,4-dioxo-3,4-dihydropyrimidin-1(2H)-yl)-N-(2-(tritylthio)ethyl)acetamide (3)

Preparation of 2-(tritylthio)ethanamine (1): To a 500 Ml round bottom flastk is charged trifluoroacetic acid (100 Ml), cysteamine (6.9 g, 89.6 mmol) and trityl chloride (25 g, 89.6 mmol). The mixture was stirred for 3 hours at room temperature. The trifluoroacetic acid was removed in vacuo and 2M NaOH (500 Ml) was added. The precipitate which formed was collected by filtration, the filtrate washed with water and hexane then dried to afford 2.4 g (80%) of the desired product as a white solid. $^1$H NMR (400 MHz, Chloroform-d) δ 7.50-7.40 (m, 6H), 7.33-7.25 (m, 6H), 7.25-7.19 (m, 3H), 2.60 (t, J=6.5 Hz, 2H), 2.33 (t, J=6.5 Hz, 2H), 1.08 (s, 2H). $^{13}$C NMR (101 MHz, Chloroform-d) δ 145.01, 129.70, 127.97, 126.75, 66.64, 41.20, 36.47. Mass: $C_{21}H_{21}NS[M+H]^+$ Calculated: 319.1395, Found: 319.1527.

Preparation of N-(2-(tritylthio)ethyl)prop-2-en-1-amine (2): To a 500 Ml flask is added THF (100 Ml) and 2-(tritylthio)ethanamine, 1, (8.6 g, 26.8 mmol) and triethylamine (8 Ml). Allylbromide (3.0 Ml, 23.8 mmol) was added dropwise. The mixture was stirred overnight then filtered. The clear solution was purified over silica (hexane/ethyl acetate 1:2) to afford 3.79 g (45%) of the desired product as a yellow oil. $^1$H NMR (400 MHz, Chloroform-d) δ 7.50-7.37 (m, 6H), 7.32-7.27 (m, 6H), 7.24-7.19 (m, 3H), 5.15-5.01 (m, 2H), 3.11 (dt, J=6.0, 1.5 Hz, 2H), 2.56 (t, J=6.7 Hz, 2H), 2.39 (t, J=6.6 Hz, 2H), 1.24 (s, 1H). $^{13}$C NMR (101 MHz, CDCl$_3$) δ 144.97, 136.74, 129.70, 127.98, 126.73, 116.00, 66.63, 51.98, 47.66, 32.40. Mass: $C_{24}H_{25}NS[M+H]^+$ Calculated: 360.1781, Found: 360.1790.

Preparation of N-allyl-2-(5-methyl-2,4-dioxo-3,4-dihydropyrimidin-1(2H)-yl)-N-(2-(tritylthio)ethyl)acetamide (3): To a 500 Ml round bottom flask is charged N-(2-(tritylthio)-ethyl)prop-2-en-1-amine, 2, (1.18 g (3.2 mmol) and dicloromethane (50 Ml). Thymine acetic acid (604 mg (3.2 mmol) was added and the solution stirred to dissolve all the solids. EDC HCl (916.8 mg 4.8 mmol) and HOBt (864 mg, 6.4 mmol) were added and the solutions stirred overnight. The solution was diluted with dichloromethane (100 Ml) then washed with brine (200 Ml). The organic layer was dried of sodium sulfate and evaporated to dryness. The crude product was purified over silica (dichloromethane/MeOH 20:1) to afford 1.26 g (75%) of the desired product as a white powder. $^1$H NMR (400 MHz, Chloroform-d) δ 8.98 (s, 1H), 7.50-7.36 (m, 6H), 7.35-7.27 (m, 5H), 7.26-7.18 (m, 4H), 6.89 (dq, J=17.5, 1.2 Hz, 1H), 5.71-5.49 (m, 1H), 5.20-4.99 (m, 2H), 4.36 (s, 1H), 4.18 (s, 1H), 3.81-3.57 (m, 2H), 3.08 (q, J=7.4 Hz, 2H), 2.58-2.36 (m, 2H), 1.90 (d, J=1.2 Hz, 3H). $^{13}$C NMR (101 MHz, CDCl$_3$) δ 166.56, 166.02, 164.24, 164.20, 151.07, 150.98, 144.72, 144.47, 141.13, 141.00, 132.31, 132.10, 129.74, 129.69, 128.22, 128.12, 128.06, 127.14, 126.88, 118.18, 117.16, 110.67, 110.58, 67.67, 67.19, 50.20, 48.57, 47.87, 47.81, 46.74, 46.17, 30.31, 29.70, 12.46. Mass: $C_{31}H_{31}N_3O_3S$ $[M+H]^+$ Calculated: 525.2892, Found: 525.1086.

Scheme II below outlines the preparation of a non-limiting example of a Type B monomer (thiol-ene) as described in Example 2.

Scheme II

4

Reagents and conditions: EDC, HOBt; rt, 18 hr.

Example 2

N-allyl-2-(6-amino-9H-purin-9-yl)-N-(2-(tritylthio) ethyl)acetamide (4)

Preparation of N-allyl-2-(6-amino-9H-purin-9-yl)-N-(2-(tritylthio)ethyl)acetamide (4): To a 250 Ml flask is charged N-(2-(tritylthio)-ethyl)prop-2-en-1-amine, 2, (900 mg, 2.5 mmol), adenine acetic acid (532 mg, 2 mmol) and dicloromethane (30 Ml). The solution is stirred to dissolve all the solids. EDC HCl (477 mg 2.5 mmol) and HOBt (612 mg, 4.0 mmol) were added and the solutions stirred overnight. The solution was diluted with dichloromethane (100 Ml) then washed with brine (200 Ml). The organic layer was dried of sodium sulfate and evaporated to dryness. The crude product was purified over silica (dichloromethane/MeOH 20:1) to afford 414 mg (39%) of the desired product as a white powder. $^1$H NMR (400 MHz, Chloroform-d) δ 8.30 (d, J=12.7 Hz, 1H), 7.85 (d, J=23.5 Hz, 1H), 7.51 -7.35 (m, 6H), 7.32-7.15 (m, 9H), 5.75-5.51 (m, 3H), 5.26-4.99 (m, 2H), 4.88 (s, 1H), 4.68 (s, 1H), 3.81-3.67 (m, 2H), 3.25-3.04 (m, 2H), 2.68-2.56 (m, 1H), 2.47 (dd, J=8.3, 6.5 Hz, 1H). $^{13}$C NMR (101 MHz, CDCl$_3$) δ 166.08, 165.56, 155.48, 155.46, 153.14, 150.39, 144.73, 144.53, 141.77, 132.37, 132.13, 129.76, 128.25, 128.09, 127.18, 126.91, 119.12, 118.39, 117.37, 67.77, 67.24, 50.52, 48.70, 46.83, 46.43, 43.85, 43.78, 30.34, 29.74. Mass: $C_{31}H_{30}N_6OS[M+H]^+$ Calculated: 535.2275, Found: 535.2288z.

Scheme III below outlines the preparation of a non-limiting example of a Type B monomer (thiol-ene) as described in Example 3.

Scheme III

Reagents and conditions: dibromoethane, $K_2CO_3$, DMF; rt, 18 hrs.

Reagents and conditions: triethylamine, acetonitrile; 60° C., 18 hrs.

Reagents and conditions: triethylamine, dichloromethane; rt, 18 hrs.

Example 3

N-(2-(6-amino-9H-purin-9-yl)ethyl)-N-(2-(tritylthio)ethyl)acrylamide (7)

Preparation of 9-(2-bromoethyl)-9H-purin-6-amine (5): To a 1000 Ml flask is added adenine (5.37 Ml, 79.8 mmol) and DMF (400 Ml). The solution is stirred and 1,2-dibromomethane (5.37 Ml, 79.8 mmol) and $K_2CO_3$ (6 g, 43.4 mmol) were added. The resulting solution is stirred overnight. The solution is then filtered and the solvent removed in vacuo to yield a solid that is dissolved in dichloromethane and washed with brine (200 Ml×2). The organic layer is dried over sodium sulfate and the solvent removed in vacuo. The crude product is purified over silica (MeOH/DCM 1:10) to afford 1.36 g (30%) of the desired product as a white solid. $^1$H NMR (400 MHz, DMSO-d) δ 8.18 (s, 1H), 8.16 (s, 1H), 7.30 (s, 2H), 4.57 (t, J=6.1 Hz, 2H), 3.94 (t, J=6.1 Hz, 2H). $^{13}$C NMR (101 MHz, DMSO-d) δ 156.05, 152.56, 149.57, 141.02, 118.79, 44.76, 40.25, 40.04, 39.83, 39.62, 39.41, 39.20, 38.99, 31.67. Mass: $C_7H_8N_5Br[M+H]^+$ Calculated: 242.0036, Found: 242.0035.

Preparation of 9-(2-((2-(tritylthio)ethyl)amino)ethyl)-9H-purin-6-amine (6): To a 100 Ml round bottom flask is charged 2-(tritylthio)ethanamine, 1, (1.28 g, 4 mmol), 9-(2-bromoethyl)-9H-purin-6-amine, 5, (970 mg, 4 mmol) and acetonitrile (50 Ml). the solution is stirred and triethylamine (1.26 Ml, 8 mmol) is added and the solution is stirred overnight at 60° C. The solvent is removed in vacuo and the crude residue taken up in dichloromethane (50 Ml) and washed with brine (200 Ml×2). The organic layer is dried over sodium sulfate, concentrated and the residue purified over silica (MeOH/DCM 1:8) to afford 1.2 g (62%) of the desired product as a white solid. $^1$H NMR (400 MHz, Chloroform-d) δ 8.33 (s, 1H), 7.85 (s, 1H), 7.44-7.36 (m, 6H), 7.31-7.26 (m, 6H), 7.24-7.14 (m, 3H), 5.62 (s, 2H), 4.19 (t, J=5.8Hz, 2H), 2.88 (t, J=5.8Hz, 2H), 2.51 (t, J=6.5 Hz, 2H), 2.35 (t, J=6.5 Hz, 2H). $^{13}$C NMR (101 MHz, Chloroform-d) δ 155.60, 152.99, 150.11, 144.87, 141.24, 129.67, 128.01, 126.80, 119.58, 66.74, 48.31, 47.95, 44.04, 32.32. Mass: $C_{28}H_{28}N_6S[M+H]^+$ Calculated: 481.2174, Found: 481.2182.

Preparation of N-(2-(6-amino-9H-purin-9-yl)ethyl)-N-(2-(tritylthio)ethyl)-acrylamide (7): To a 50 Ml flask is added 9-(2-((2-(tritylthio)ethyl)amino)ethyl)-9H-purin-6-amine, 6, (100 mg, 0.21 mmol), triethylamine (56 µL, 0.4 mmol) and dichloromethane (10 Ml). Acryloyl chloride (24 µL, 0.30 mmol) was added dropwise and the solution stirred overnight. Aqueous $NaHCO_3$ was added to quench the reaction and the organic layer was washed with brine (200 Ml×2). The organic layer is dried over sodium sulfate, concentrated and the residue purified over silica (MeOH/DCM 1:20) to afford 87 mg (78%) of the desired product as a white solid. $^1$H NMR (400 MHz, DMSO-d6) δ 8.10 (dd, J=7.4, 1.3 Hz, 1H), 7.98 (s, 1H), 7.42-7.10 (m, 17H), 6.17 (ddd, J=96.4, 16.6, 10.2 Hz, 1H), 5.88 (ddd, J=33.4, 16.5, 2.5 Hz, 1H), 5.43 (ddd, J=60.9, 10.2, 2.5 Hz, 1H), 4.15 (dt, J=17.3, 6.0 Hz, 2H), 3.51 (q, J=8.1, 7.1 Hz, 2H), 3.04 (dt, J=51.0, 7.5 Hz, 2H), 2.32 (dt, J=24.5, 7.3 Hz, 2H). $^{13}$C NMR (101 MHz, DMSO) δ 165.25, 165.05, 155.94, 155.90, 153.18, 152.54, 152.36, 149.66, 149.59, 144.37, 144.25, 140.76, 140.68, 129.14, 128.10, 128.07, 127.73, 127.61, 127.47, 127.27, 126.97, 126.88, 126.78, 118.61, 118.59, 66.67, 66.33, 46.84, 46.66, 45.62, 44.83, 41.60, 40.76, 40.14, 30.53, 29.08. Mass: $C_{31}H_{30}N_6OS[M+H]^+$ Calculated: 535.2275, Found: 535.2265.

Scheme IV

Reagents and conditions: triphenylmethanethiol, DBU, DMF; rt, 18 hr.

Reagents and conditions: EDC, HOBt, DCM; rt, 18 hr.

Example 4

2-(5-methyl-2,4-dioxo-3,4-dihydropyrimidin-1(2H)-yl)-N,N-bis(2-(tritylthio)ethyl)acetamide Preparation off bis(2-(tritylthio)ethyl)amine (8): To a 250 Ml flask is charged with DBU (10.0 Ml, 67.2 mmol) and a solution of bis(2-chloroethyl)amine hydrochloride (3.0 g, 16.8 mmol) and triphenylmethanethiol (9.3 g, 33.6 mmole) in anhydrous dimethylformamide (50 Ml). The reaction mixture was stirred overnight at room temperature and then the solvent was removed in vacuo. The crude product was taken up in dichloromethane (50 Ml) and washed with brine (200 Ml×2). The solvent was removed and the crude product purified over silica (DCM/MeOH 20:1) to afford 6.58 g (57%) of the desired product as a white solid. $^1$H NMR (400 MHz, Chloroform-d) δ 7.42-7.35 (m, 12H), 7.29-7.16 (m, 18H), 2.36 (t, J=6.9 Hz, 4H), 2.25 (t, J=6.9, 4H). $^{13}$C NMR (101 MHz, CDCl$_3$) δ 145.00, 129.73, 128.01, 126.76, 66.68, 47.91, 32.35. Mass: C$_{42}$H$_{39}$NS$_2$[M+H]$^+$ Calculated: 622.2602, Found: 622.2600.

Preparation of 2-(5-methyl-2,4-dioxo-3,4-dihydropyrimidin-1(2H)yl)-N,N-bis(2-(tritylthio)ethyl)acetamide (9): Thymine acetic acid (736 mg, 4.0 mmol) and bis(2-(tritylthio)ethyl)amine, 8, (1.86 g, 3.0 mmol) of 8 were dissolved in dichloromethane (20 Ml). EDC HCl (1.2 g, 4 mmol) and HOBt (920 mg, 6 mmol) were added and the solutions was stirred at room temperature overnight. The reaction mixture was washed with brine, concentrated and the crude product purified over silica (DCM/MeOH 20:1) to afford 1.65 g (68%) of the desired product as a white powder. $^1$H NMR (400 MHz, Chloroform-d) δ 8.24 (s, 1H), 7.43-7.33 (m, 12H), 7.32-7.26 (m, 10H), 7.25-7.17 (m, 8H), 6.75 (q, J=0.9 Hz, 1H), 3.96 (s, 2H), 2.79-2.65 (m, 4H), 2.41-2.28 (m, 2H), 2.23 (t, J=7.4 Hz, 2H), 1.87 (s, 3H). $^{13}$C NMR (101 MHz, CDCl$_3$) δ 165.96, 164.04, 150.77, 144.72, 144.48, 141.02, 129.77, 129.69, 128.24, 128.19, 128.09, 127.18, 126.93, 110.55, 77.48, 77.36, 77.16, 76.84, 67.62, 67.13, 47.68, 46.91, 45.88, 30.40, 29.32, 12.48. Mass: C$_{49}$H$_{45}$N$_3$O$_3$S$_2$[M+Na]$^+$ Calculated: 810.2800, Found: 810.2799.

Scheme v below outlines the preparation of a non-limiting example of a Type B monomer (thiol-ene) as described in Example 5.

Scheme V

Reagents and conditions: TEA, DCM; rt, 18 hr.

Reagents and conditions: K$_2$CO$_3$, DMF; rt, 18 hr.

Example 5

N,N-diallyl-2-(6-amino-9H-purin-9-yl)acetamide (11)

Preparation of diallylcarbamic bromide (10): Bromoacetic bromide (742 µL, 10 mmol) was added dropwise to a solution of diallyl amine (1.23 Ml, 10 mmol) in DCM (20 Ml). The mixture was stirred at room temperature overnight. After that, the solution was washed with brine and dried over sodium sulfate, removal of the solvent in vacuo afforded 1.7 g of yellow oil. This product was used without further purification.

Preparation of N,N-diallyl-2-(6-amino-9H-purin-9-yl)acetamide (11): The crude diallylcarbamic bromide, 10, (326 mg, 1.5 mmol) was dissolved in DMF (10 Ml) and then adenine (202 mg, 1.5 mmol) and Na$_2$CO$_3$ (207 mg, 1.5 mmol) were added and the solution stirred at room temperature overnight. The solvent was removed and the residue taken up in DCM (20 Ml) and washed with brine then dried over sodium sulfate. The solvent was removed and the crude product was purified over silica (DCM/MeOH 10:1) to afford 285 mg (70%) of the desired product as a white solid. $^1$H NMR (400 MHz, Chloroform-d) δ 8.34 (s, 1H), 7.94 (s, 1H), 5.94-5.63 (m, 4H), 5.37-5.10 (m, 4H), 5.02 (s, 2H), 4.05 (tt, J=5.8, 1.6 Hz, 4H). $^{13}$C NMR (101 MHz, CDCl$_3$) δ 166.12, 155.55, 153.19, 150.44, 141.78, 132.39, 132.19, 118.69, 117.75, 49.17, 49.06, 43.98. Mass: C$_{13}$H$_{16}$N$_6$O[M+H]$^+$ Calculated: 273.1464, Found: 273.1469.

Scheme VI below outlines the preparation of a non-limiting example of a Type B monomer (thiol-ene) as described in Example 6.

Reagents and conditions: K$_2$CO$_3$, DMF; acetonitrile rt, 18 hr.

Reagents and conditions: acryloyl chloride, TEA, DCM; rt, 18 hr.

Example 6

N-(2-(6-amino-9H-purin-9-yl)ethyl)-N-allyl)acrylamide (13)

Preparation of 9-(2-(allyl)amino)ethyl)-9H-purin-6-amine (12): To a 100 Ml flask is charged 9-(2-bromoethyl)-9H-purin-6-amine, 5, (508 mg, 2.1 mmol), allylamine (1 Ml) and acetonitrile (10 Ml). K$_2$CO$_3$ (437 mg, 3.2 mmol) was added and the mixture was stirred at 50° C. overnight. The reaction solution was concentrated in vacuo and the residue was taken up in dichloromethane (20 Ml) and washed with brine (50 Ml×2). The organic layer was dried over sodium sulfate, the solvent removed and the residue purified over silica (MeOH/DCM 1:5) to afford 277 mg (60%) of the desired product as a white solid. $^1$H NMR (400 MHz, Chloroform-d) δ 8.36 (s, 1H), 7.91 (s, 1H), 5.82 (ddt, J=17.3, 10.2, 6.0 Hz, 1H), 5.69 (s, 2H), 5.19-5.01 (m, 2H), 4.30 (dd, J=6.2, 5.6 Hz, 2H), 3.26 (dt, J=6.0, 1.4 Hz, 2H), 3.08 (dd, J=6.3, 5.5 Hz, 2H). $^{13}$C NMR (101 MHz, CDCl$_3$) δ 155.61, 153.08, 150.29, 141.26, 136.39, 119.81, 116.51, 52.07, 48.22, 44.29.

Preparation of N-(2-(6-amino-9H-purin-9-yl)ethyl)-N-allyl)acrylamide (13): To a 100 Ml flask is charge 9-(2-(allyl)amino)ethyl)-9H-purin-6-amine, 12, (277 mg, 1.27 mmol), triethylamine (355 μL, 2.54 mmol) and dichloromethane (20 Ml). Acryloyl chloride (102 Ml, 1.27 mmol) was added dropwise and the mixture was stirred overnight. Then saturated NaHCO$_3$(aq) was added to quench the reaction and the organic layer was washed by brine (40 Ml×2) then dried by sodium sulfate. The solvent was removed and the residue was purified over silica (DCM/MeOH 20:1) to afford 256 mg (83%) of the desired product as a white solid. $^1$H NMR (400 MHz, Chloroform-d) δ 8.34 (s, 1H), 7.75 (s, 1H), 6.46-6.26 (m, 2H), 5.99 (d, J=14.6 Hz, 2H), 5.69 (dd, J=9.2, 3.1 Hz, 1H), 5.55 (ddt, J=17.1, 9.9, 4.9 Hz, 1H), 5.11-4.93 (m, 2H), 4.48 (t, J=6.2 Hz, 2H), 3.81 (t, J=6.2 Hz, 2H), 3.65 (dt, J=4.9, 1.8 Hz, 2H). $^{13}$C NMR (101 MHz, CDCl$_3$) δ 167.32, 155.70, 153.20, 150.25, 141.07, 140.31, 132.95, 132.25, 129.48, 129.08, 127.26, 126.29, 119.84, 118.33, 117.52, 51.81, 50.72, 49.20, 47.07, 46.37, 42.99, 41.82. Mass: C$_{13}$H$_{16}$N$_6$O[M+H]$^+$ Calculated: 273.1464, Found: 273.1471.

Scheme VI below outlines the preparation of a non-limiting example of a protected Type A monomer (thiol-Michael) as described in Example 7.

Reagents and conditions: tert-butyl bromoacetate, CsCO$_3$, K$_2$CO$_3$, DMF; rt, 36 hr

19

-continued

14

Reagents and conditions: triethylsilane, TFA, DMF; 0° C. - rt, 5 hr

16

Reagents and conditions: EDC, HOBt, DCM; rt, 18 hr.

Example 7

N4-Benzoylcytosine-N-(2-(tritylthio)ethyl)acetamide (16)

Preparation of N4-Benzoylcytosine acetic acid t-butyl ester (14): To as suspension of N4-benzoylcytosine (1.0 g, 4.65 mmol) in DMF was added potassium carbonate (643 mg, 4.65 mmol) and cesium carbonate (151 mg, 0.46 mmol). The solution was stirred for 30 minutes after which tert-butyl bromoacetate (0.75 Ml, 5.11 mmol) was added dropwise and the reaction mixture was allowed to stir for 36 hours. The solution was then filtered through Celite and the filtrate concentrated in vacuo. The crude material was triturated with ethyl acetate (50 Ml) and the desired product 1.038 g (68%) was collected by filtration as a white solid. $^1$H NMR (400 MHz, DMSO-d6) δ 11.21 (br s, 1H), 8.09 (d, J=7.3 Hz, 1H), 8.06-7.98 (m, 2H), 7.63 (t, J=4 Hz, 1H), 7.52 (t, J=8 Hz, 2H), 7.29 (d, J=7.3 Hz, 1H), 4.56 (s, 2H), 1.43 (s, 9H). $^{13}$C NMR (101 MHz, DMSO-d6) δ 167.48, 133.01, 128.91, 128.84, 96.62, 82.20, 51.65, 28.16.

Preparation of N4-Benzoylcytosine acetic acid (15): To a suspension of N4-benzoylcytosine acetic acid t-butyl ester, 14, (1.0 g, 3.04 mmol) in dry DCM (10 Ml) was added triethylsilane (2.4 Ml, 15.1 mmol). The reaction solution was cooled to 0° C., TFA (7.5 Ml) was added dropwise and the reaction mixture was stirred at room temperature for 5 hours. After completion of the reaction, the solvent was evaporated off by purging with air in a fume hood and the residue was boiled with ether. The desired product (814 mg, 98%) was obtained by filtration as a white solid. $^1$H NMR (400 MHz, DMSO-d6) δ 13.13 (br s, 1H), 11.26 (br s, 1H), 8.15 (d, J=7.3 Hz, 1H), 8.05-7.98 (m, 2H), 7.63 (ddt, J=8.1, 6.8, 1.3 Hz, 1H), 7.57-7.48 (m, 2H), 7.33 (d, J=7.2 Hz, 1H), 4.59 (s, 2H). $^{13}$C NMR (101 MHz, DMSO-d6) δ 169.77, 163.96, 151.15, 133.65, 133.18, 128.90, 96.33, 51.07.

Preparation of N4-Benzoylcytosine-N-(2-(tritylthio)ethyl)acetamide (16): To a suspension of the cytosine acetic acid, 15, (362 mg, 1.32 mmol) in dry DMF (5 Ml) were added HOBt (223 mg, 1.65 mmol), EDC.HCl (316 mg, 1.65 mmol) and N-(2-(tritylthio)ethyl)-prop-2-en-1-amine, 2, (500 mg, 1.39 mmol). Triethylamine (0.405 Ml, 2.90 mmol) was added to the reaction mixture and the reaction solution stirred at room temperature for 12 hours. The solvent was removed in vacuo and the residue was dissolved in DCM (50 Ml). The organic layer was washed thoroughly with water (2×30 Ml) and brine (30 Ml), dried over sodium sulfate and purified over silica (0-7% MeOH in DCM) to afford 603 mg (74%) of the desired product as a white solid. $^1$H NMR (400 MHz, CHCl$_3$-d) δ 8.76 (br s, 1H), 7.92 (d, J=7.7 Hz, 2H), 7.71-7.58 (m, 2H), 7.58-7.46 (m, 3H), 7.47-7.38 (m, 6H), 7.38-7.19 (m, 9H), 5.75-5.51 (m, 1H), 5.25-5.00 (m, 2H), 4.61 (s, 1H), 4.42 (s, 1H), 3.76 (dd, J=5.9, 1.5 Hz, 1H), 3.74-3.66 (m, 1H), 3.20 (t, J=7.5 Hz, 1H), 3.15-3.03 (m, 1H), 2.69-2.54 (m, 1H), 2.54-2.41 (m, 1H). $^{13}$C NMR (101 MHz, CHCl$_3$-d) δ 172.25, 166.27, 165.73, 162.56, 150.01, 144.63, 144.42, 133.17, 132.29, 132.18, 129.65, 129.62, 129.03, 128.15, 128.11, 127.95, 127.58, 127.01, 126.76, 117.97, 117.08, 67.56, 67.09, 53.43, 50.34, 49.53, 49.32, 48.67, 46.77, 46.36, 30.32, 29.54. Mass: C37N34N4O$_3$S [M+H]$^+$ 615.2430, Found: 615.2893.

Scheme VII below outlines the general procedure for the de-protection of thiol groups as described in Example 8.

Scheme VIII

Reagents and conditions: TFA/TES/DCM; rt, 15-20 min.

Example 8

General Procedure for Deprotection of STrt

The S-trityl onomer (1 mmol) is dissolved in TFA/TES/DCM (1:1:3) 8 Ml and the mixture stirred at room temperature for 15-20 mins. The solvent is removed and the crude product is dissolved in fresh DCM, washed with NaHCO$_3$ and purified over silica.

Scheme IX below outlines the general procedure for the formation of the disclosed dimers, trimers and tetramers as described in Example 9.

Scheme IX

Reagents and conditions: DBU, DCM; rt 1 hr.

Example 9

General Procedure for Oligomer Synthesis

A deprotected Type B monomer (thiol-ene) (0.05 mmol) and a protected Type A monomer (thiol-Michael) (0.5 mmol) are dissolved in DCM (3 Ml) and DBU (20 μL) was added. The mixture is stirred at room temperature for 1 hour. The crude product is purified over silica (DCM:Methanol 10:1) to afford the corresponding dimer which can be confirmed by MALDI-TOF.

To form a trimer, the Type A residue of the dimer is de-protected according to Example 8 and the procedure above repeated. If a tetramer is desired, these two steps are repeated until the desired trimer or tetramer is obtained.

The following is a non-limiting example of a dimer prepared according to the disclosed procedures.

Figure 1:
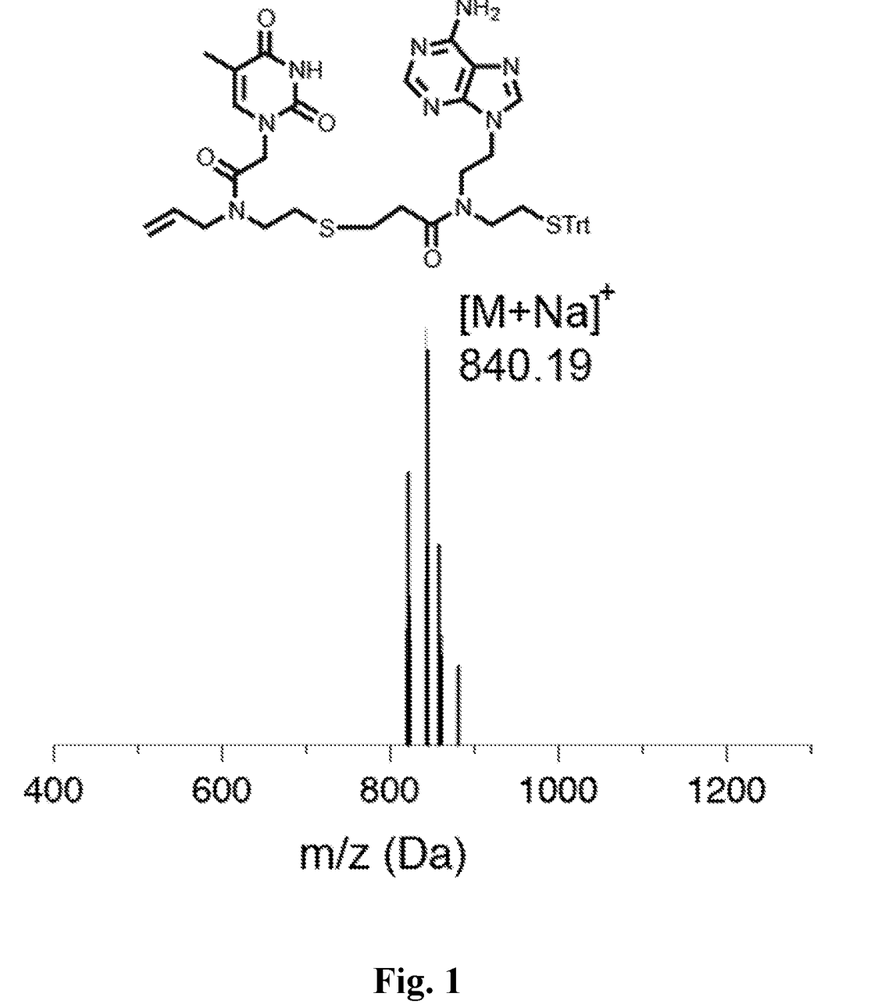
FIG. 1 is the MALDI-TOF mass spectrum of a dimer according to the present disclosure which can be polymerized. Alternatively, the dimer can be further reacted to prepare a trimer or tetramer as described herein.

FIG. 1 shows the MALDI-TOF spectrum of this dimer.

The following is a non-limiting example of a trimer prepared according to the disclosed procedures.

Figure 2:
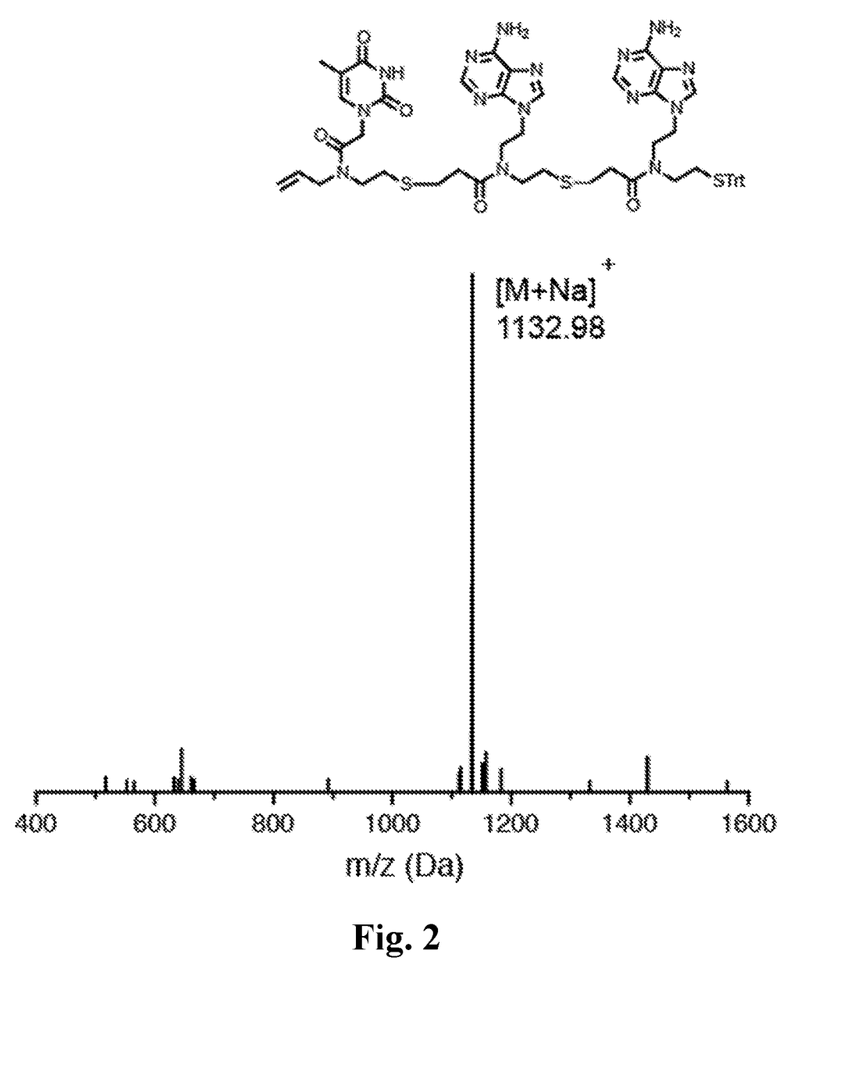
FIG. 2 is the MALDI-TOF mass spectrum of a trimer according to the present disclosure which can be polymerized as described herein to form an antisense polymer for use in treating a trinucleotide repeat disorder. Alternatively, the trimer can be further reacted to prepare a tetramer or repeating oligomer CNA-polymer as described herein.

FIG. 2 shows the MALDI-TOF spectrum of this trimer.

Scheme X below outlines the general procedure for the polymerization of the disclosed dimers, trimers and tetramers as described in Example 10.

Scheme X

Reagents and conditions: UV 365 nm, DMPA, CHCl₃; 30 min.

Example 10

General Procedure for Polymerization of Oligomers

[This example illustrates the polymerization of a dimer as formed in Example 9. The following procedure can be performed equally well with a trimer or tetramer, by substituting a trimer or tetramer in the following example.]

A de-protected dimer (1 mmol) and 2,2-dimethoxy-2-phenylacetophenone (DMPA) (4 mg) were dissolved into CDCl₃, (0.8 Ml). The solution is then the irradiated by a UV lamp at 365 nm for 30 minutes. At this point the solution is analyzed by $^1$H-NMR to verify the formation of the oligomer. After this reaction time, a white precipitate has formed. The liquid fraction is decanted, and the precipitate then rinsed with diethyl ether (4×3 Ml). Filtration and drying yield a white solid, wherein the product is subjected to MALDI-TOF and NMR analyses to confirm the structure.

Example 11

General Procedure for Polymerization of Dimers utilizing Type C Monomers

A stoiciometric mixture of a de-protected Type D/Type A dimer (1 mmol), and a type C monomer (1 mmol) and 2,2-dimethoxy-2-phenylacetophenone (DMPA) (4 mg) were dissolved into CDCl₃, (0.8 mL). The solution is then the irradiated by a UV lamp at 365 nm for 30 minutes. At this point the solution is analyzed by $^1$H-NMR to verify the formation of the oligomer. After this reaction time, a white precipitate has formed. The liquid fraction is decanted, and the precipitate then rinsed with diethyl ether (4×3 mL). Filtration and drying yield a white solid, wherein the product is subjected to MALDI-TOF and NMR analyses to confirm the structure.

In a like manner Type D monomers can be used to form dimers that can be reacted with Type B/Type D dimers

METHODS

Disclosed herein are method for treating diseases caused by trinucleotide repeat disorders. Currently, there are up to fourteen neurologic disorders identified as being caused by an increased number of CAG repeats, typically in coding regions of otherwise unrelated proteins. During protein synthesis, the expanded CAG repeats are translated into a series of uninterrupted glutamine residues forming what is known as a polyglutamine tract ("polyQ"). These polyglutamine tracts may be subject to increased aggregation

In addition, poly(CAG) repeats need not always be translated in order to cause toxicity. A protein known to bind CUG repeats (muscleblind, or mbl) is also capable of binding CAG repeats. When the CAG repeat was changed to a repeating series of CAACAG (which also translates to polyQ), toxicity was dramatically reduced (See, Li, L et al., (2008). "RNA toxicity is a component of ataxin-3 degeneration in Drosophila," Nature. 453 (7198) (2008)): The human homolog of mbl, MBNL1, which was originally identified as binding CUG repeats in RNA, also binds CAG and CCG repeats as well.

Huntington's disease causes the HTT gene to expand the sequence poly(CAG). The disclosed antisense CNA-polymers can be used to inhibit the HTT expression of the poly(CAG) sequence. SBMA (Spinobulbar Muscular Atrophy), a manifestation of Huntington's disease, occurs predominantly in males and is characterized by weakness and atrophy of the proximal muscles. Difficulties with swallowing and articulating speech are also common symptoms of SBMA. As the first word of its name implies, the disease mainly affects the spinal cord ("spino-") and a part of the brain called the bulbar region ("-bulbar").

Therefore, disclosed herein is a method for treating a neurological disorder caused by excessive poly trinucleotide repeats, comprising contacting a subject in need of treatment with a disclosed CNA-polymer.

PROCESS

Disclosed herein is a process for preparing the disclosed CNA-polymers. The process comprises:
A) combining a protected Type A monomer having the formula:

with a Type B monomer having the formula:

to form a compound having the formula:

B) de-protecting the thiol unit to form an oligomer having the formula:

C) optionally repeating steps (a) to (b) for from 1 to 19 additional times with the same or different Type A monomer; or

D) treating the oligomer formed in step (b) to form a CNA-polymer having the formula:

wherein each NB is the same or different nucleobase, the index m is an integer from 1 to 20 and n is an integer from 0 to 100.

What is claimed is:

1. A Click Nucleic Acid polymer (CNA) having the formula:

wherein each NB is the same or different nucleobase, the index m is an integer from 1 to 20 and n is an integer from 0 to 100.

2. The CNA-polymer according to claim 1, wherein the nucleobase is chosen from cytosine, guanine, adenine, thymine, uracil, 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, β-D-galactosyl-queosine, inosine, 1-methylguanine, 1-methylinosine, 2,2-dimethylguanine, 2-methyladenine, 2-methylguanine, 3-methylcytosine, 5-methyl-cytosine, $N^6$-adenine, 7-methylguanine, 5-methylaminomethyluracil, methoxyamino-methyl-2-thiouracil, beta-D-mannosylqueosine, 5'-methoxycarboxy-methyluracil, 5-methoxyuracil, 2-methylthio-$N^6$-isopentenyladenine, uracil-5-oxyacetic acid, pseudo-uracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-$N^2$-carboxypropyl)uracil, or 2,6-diaminopurine.

3. The CNA-polymer according to claim 1, wherein the nucleobase is chosen from cytosine, guanine, adenine, thymine, or uracil.

4. The CNA-polymer according to claim 1, wherein the index m is an integer from 1 to 5.

5. The CNA-polymer according to claim 4, wherein the index m is an integer from 1 to 4.

6. The CNA-polymer according to claim 5, wherein the index m is an integer from 1 to 3.

7. The CNA-polymer according to claim 6, wherein the index m is an integer from 1 to 2.

8. The CNA-polymer according to claim 1, wherein the index n is an integer from 1 to 100.

9. The CNA-polymer according to claim 8, wherein the index n is an integer from 1 to 50.

10. The CNA-polymer according claim 9, wherein the index n is an integer from 1 to 20.

11. The CNA-polymer according to claim 10, wherein the index n is an integer from 1 to 10.

12. The CNA-polymer according to claim 11, wherein the index n is an integer from 1 to 8.

13. The CNA-polymer according to claim 12, wherein the index n is an integer from 1 to 6.

14. The CNA-polymer according to claim 13, wherein the index n is an integer from 1 to 4.

15. The CNA-polymer according to claim 1, comprising one or more antisense codons having the formula:

16. The CNA-polymer according to claim 1, comprising one or more antisense codons having the formula:

17. The CNA-polymer according to claim 1, comprising one or more antisense codons having the formula:

18. A CNA-polymer according to claim 1, having the formula:

wherein the index n is an integer from 0 to 20.

19. A CNA-polymer having the formula:

wherein the index n is an integer from 0 to 20.

20. A CNA-polymer having the formula:

wherein the index n is an integer from 0 to 20.

* * * * *